United States Patent
Hirsch (12)

(10) Patent No.: US 6,506,928 B1
(45) Date of Patent: Jan. 14, 2003

(54) DENDRIMERIC FULLERENE DERIVATIVES, PROCESS FOR THEIR PREPARATION, AND USE AS NEUROPROTECTANTS

(75) Inventor: Andreas Hirsch, Erlangen (DE)

(73) Assignee: Siemens Axiva GmbH & Co. KG (DE)

(*) Notice: Subject to any disclaimer, the term of this patent is extended or adjusted under 35 U.S.C. 154(b) by 0 days.

(21) Appl. No.: 09/622,777

(22) PCT Filed: Jan. 23, 1999

(86) PCT No.: PCT/EP99/00439

§ 371 (c)(1),
(2), (4) Date: Aug. 31, 2000

(87) PCT Pub. No.: WO99/43358

PCT Pub. Date: Sep. 2, 1999

(30) Foreign Application Priority Data

Feb. 25, 1998 (DE) .......................................... 198 07 979

(51) Int. Cl.$^7$ ............................................. C07C 69/76
(52) U.S. Cl. ................................ 560/80; 560/76; 560/8
(58) Field of Search ................................. 560/80, 76, 8

(56) References Cited

PUBLICATIONS

Nierengarten et al. Helvetica Chimica Acta, 1997, vol. 80 pp. 2238–2276.*
Cardullo et al, Langmuir, 1998, vol. 14, pp. 1955–1959.*
Brettreich, M., et al, *Tetrahedron Letters* 39:2731–2734, XP–002105119, (1998).
Dugan, L. L., et al, *Proc. Natl. Acad. Sci. USA* 94:9434–9439, XP–002105120, (1997).
Nierengarte, J–F, et al, *Helvetica Chimica Acta* 80:2238–2276, XP–002105121, (1997).
Cardullo, F., et al, *Langmuir* 14:1955–1959, XP–002105122, (1998).
Karfunkel, H. R., et al, *US National Library of Medicine (NLM) & J Comput Aided Mol Des* 6:521–35, XP–002105123, (1992).
Chen, H. H., et al, *NLM & Toxicologic Pathology* 26:143–51, XP–002105124, (1998).
Dai, L., et al, *Chemical Abstracts Service & J. Phys. Chem. B* 102 (*21*):4049–4053, XP–002105125, (1998).

* cited by examiner

*Primary Examiner*—Paul J. Killos
*Assistant Examiner*—Hector M Reyes
(74) *Attorney, Agent, or Firm*—Connolly Bove Lodge & Hutz LLP

(57) ABSTRACT

The invention relates to dendrimeric fullerene derivatives in which the fullerene is linked to at least one dendron, wherein the or each dendron has at least one protic group which imparts water solubility.

13 Claims, No Drawings

DENDRIMERIC FULLERENE DERIVATIVES, PROCESS FOR THEIR PREPARATION, AND USE AS NEUROPROTECTANTS

The invention relates to dendrimeric fullerene derivatives, that is fullerene derivatives which are substituted by one or more dendrons. Fullerenes are carbon compounds of the formula $C_2(10+m)$, where m is a natural number. They contain twelve five-membered and any desired number, i.e. m, but at least two, six-membered rings of carbon atoms.

The outwardly vaulted surface of fullerenes and the alignment of the π electrons produced thereby cause a great reactivity to free radicals /1/ (The literature references are listed at the end of the description). Thus, it is known for $C_{60}$ Buckminsterfullerene that it very easily adds radicals. The absorption of up to 34 methyl radicals is described and the name "radical sponge" has been proposed therefor /1/.

It is known that hydroxyl and hydroperoxide radicals in biological systems preferably attack polyunsaturated fatty acids. This attack brings about crosslinking and polymerization of the fatty acid structures. Free radicals thus also bring about damage to biomembranes, in particular the membranes of nerve cells, which are distinguished by a particularly high proportion of unsaturated fatty acids in their lipids. As a result of the change in the lipid structure of such biomembranes, a change in the membrane permeabilities, a change in their transport functions, a change in their barrier mechanisms and changes in their receptor activities can occur and this can lead to the death of the nerve cells. Overstimulation of glutamate receptors likewise led to the formation of free oxygen radicals and nitric oxide radicals /2–6/ and as a result to damage to nerve cells and to the occurrence of specific syndromes /7–10/.

Radical scavengers provide for the removal of harmful free radicals, act as antioxidants and suppress the damage to the nerve cells and the loss of function of neuromembranes. Therefore, especially fullerenes with their excellent radical-scavenging properties should act as neuroprotectants and should be able to be employed for the protection of biological membranes against oxidative changes. $C_{60}$ fullerene, however, is only soluble in very few organic solvents, such as benzene and toluene, and thus cannot also be administered to biological membranes. The addition of suitable functional groups on $C_{60}$, however, should improve the water solubility and thus also make possible use as antioxidants in biological systems. The first positive results were achieved using polyhydroxylated $C_{60}$/11/, and trisubstituted synthetic malonic acid derivatives $C_{60}[C(COOH)_2]_3$, which had both in vitro and in vivo neuroprotective activities, afforded better results /12/. The preparation of the two isomers having $C_3$ or $D_3$ symmetry described in /12/ was carried out by the method of Hirsch /13/ by triple cyclopropanylation of $C_{60}$ with diethyl malonate, hydrolysis and subsequent chromatographic purification. The two test compounds exhibited strong affinity for free radicals, as it was possible to show by EPR spectroscopy, and inhibited the excitotoxic death of cell cultures of cortical neurons which were induced by N-methyl-D-aspartate (NMDA) exposure, by α-3-hydroxy-5-methyl-4-isoxazolepropionic acid (AMPA) exposure or by oxygen/glucose withdrawal. The $C_3$-symmetrical derivative moreover reduced apoptotic neural death which was induced either by serum withdrawal or exposure of $A^\beta 1$–42 protein. In all cases, the $C_3$ regioisomer exhibited greater efficacy than the $D_3$ isomer, which can be attributed to the greater polarity and thus improved ability of lipid membrane penetration /12/.

Relative to the polyhydroxy-substituted fullerenes, the malonic acid derivatives exhibited better activity as radical scavengers as it [lacuna] with the lower degree of addition and resulting from this an improved provision of a relatively large reactive surface with, at the same time, accompanying improved water solubility.

Furthermore, fullerenes are known from /17/ which are linked to poly(benzyl ether) dendrons. These fullerene derivatives, however, are insoluble in water. In /19/, dendrimeric fullerenes are likewise disclosed which are insoluble in water.

In relation to this prior art, the invention was based on the object of further improving the water solubility of fullerenes or fullerene derivatives without at the same time, as in the cases known to date, making smaller or screening off the reactive $C_{60}$ surface and thus reducing the radical-scavenging properties.

This object is achieved according to the invention by dendrimeric fullerene derivatives in which the fullerene is linked to at least one dendron, wherein the or each dendron has at least one protic group which imparts water solubility.

Another object of the invention further relates to an agent comprising the inventive fullerene for thereapeutic purposes. The invention additionally relates to an agent comprising the inventive fullerene as neuroprotectant. The inventive fullerene derivates can be used in the production of pharmaceuticals for the treatment of diseases in which free radicals have a harmful effect on the organism to be treated.

Suitable protic groups are the hydrophilic groups known to the person skilled in the art, preferably —OH, —COOH, —NH$_2$, —SO$_3$H, —PO$_3$H, NR$_4^+$, —NHOH, or —SO$_2$NH$_2$, where the four radicals R independently of one another can in each case identically or differently be —H, alkyl or aryl. —OH, —COOH and —NH$_2$ are particularly preferred. The group —COH can also be employed.

The water solubility of the fullerene derivatives according to the invention can be greater than 1 mg/ml at 25° C. and pH 7, preferably greater than 5 mg/ml, particularly preferably greater than 10 g/l and very particularly preferably greater than 20 mg/ml. At 25° C. and pH 10 it can be greater than 10 mg/ml, preferably greater than 50 mg/ml, particularly preferably greater than 100 g/l and very particularly preferably greater than 200 mg/ml.

A dendron within the meaning of the invention is an addendum of the $C_{60}$ nucleus unit which has a branching at the end as a structural unit. Again, in each case the same or another subunit, at whose other end a branching is likewise located in turn, can be linked to this. Depending on the degree of branching, the number of the nearest branchings and thus also the number of functional (and water-soluble) end groups is thus doubled, tripled or multiplied. Each radially symmetrical "shell" formed by repeated linkage of dendrons is designated as the next generation. In order to make available more reactive surface for radicals, it appears sensible to keep the dendrons necessary for the water solubility at as far a distance as possible from the $C_{60}$ core in order to prevent its "covering". This is possible by binding of the dendrons of the first generation via a so-called "spacer", i.e. a carbon chain of length $C_1$ up to about $C_{100}$, preferably $C_2$–$C_{10}$, which serves the $1^{st}$ generation as a "separator".

Suitable branchings are especially trivalent or polyvalent elements such as, for example, N-, C-, P-, Si, or polyvalent molecular segments such as aryl-, heteroaryl. The degree of branching is preferably between two and three and the number of generations can be between 1 and 10 inclusive.

Preferred solutions to the object according to the invention follow from the subclaims. Individual features or a number of the features disclosed in the subclaims can also in each case represent solutions to the underlying object per se or in combination and the individual features can also be combined in any desired manner within the claim categories.

In relation to the examples mentioned further above, monoadducts of fullerenes should be an improvement if their water solubility is adequately high. The lower the degree of addition of the fullerenes, the greater their free reactive surface will be, which appears responsible for the radical-scavenging properties. Such monoadducts, however, should have a lower water solubility in relation to polyadducts, as the number of hydrophilic groups decreases correspondingly. This conflict is solved by the fullerenes according to the invention as they in turn arbitrarily increase in water solubility owing to the branchings of the higher generations lying further outside.

A preferred compound is shown in formula 1 (Scheme 1). What are concerned here are dendrimer-branched derivatives of $C_{60}$-fullerenes. Monosubstituted dendrimers of this type offer the advantage that they retain their excellent water solubility independently of the degree of addition owing to the choice of suitable functional end groups. The number of the functions of the outermost dendrimer shell contributing to the solubility is additionally specified by the degree of branching and by the number of dendron generations (cf. section above). Branching elements of the individual molecular esters can inter alia preferably be γ-aminotriscarboxylic acids of the type shown in formula 1, α-aminodicarboxylic acids, α-ω-diaminocarboxylic acids, hydroxycarboxylic acids, tartaric acid derivatives, polyphenols, carbohydrate components of the pentose and hexose type, glycerol derivatives and also generally polyfunctional compounds. The consecutive linkages of the individual dendrimer branches or of the individual generations then corresponds to acid amide compounds, peptide compounds, ester bonds, depsipeptide-like bonds according to the nature of the variable acid amide or ester linkage of amino acids and hydroxy acids, glyceride-like bonds and polyesters or polyethers, polyphenyl ethers and glycosides. An adverse effect of the free fullerene surface due to screening is only expected in the case of dendrimer shells of the third generation, screening on account of easy penetrability of small free radicals, nevertheless does not necessarily have to lead to a decrease in the antioxidant activity. Owing to the choice of suitable lengths of two up to six carbon atoms in the spacer chains, the availability of the fullerene surface can additionally be varied or guaranteed. The use of long fatty acid chains in the individual branches can additionally bring about an affinity for the fatty acid chains of the lipids within the membrane bilayer and thus improved intercalation in nerve membranes and improved radical-scavenging properties.

Scheme 1

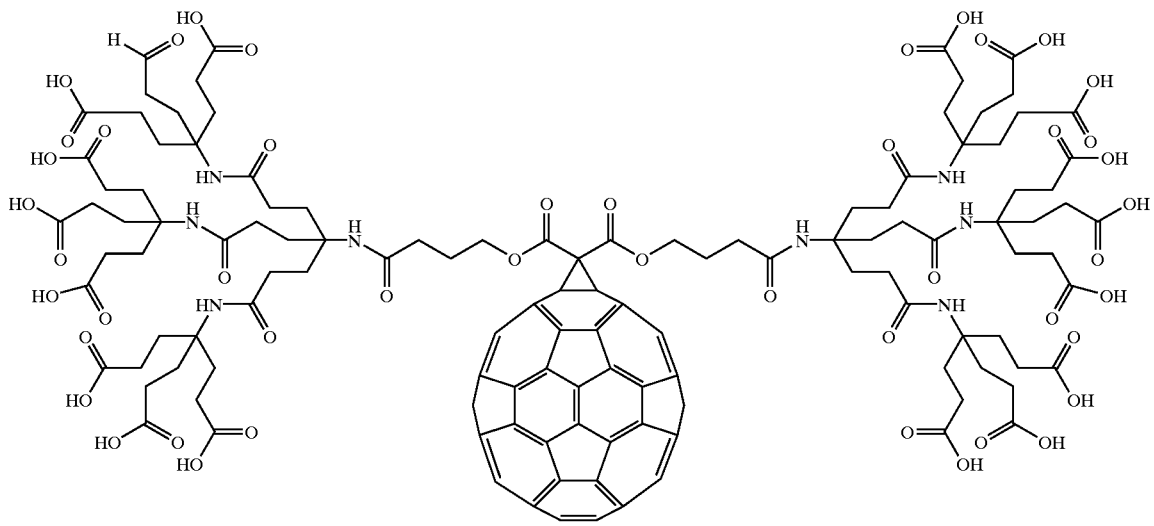

1

The preparation of the target compounds is carried out by convergent synthesis, i.e. the corresponding dendrimer branch is synthesized separately up to the first, second, third or nth generation and only finally bonded to $C_{60}$ fullerene by means of a suitable linkage reaction, such as, for example, a cyclopropanylation, Diels-Alder reaction, [3+2] cycloaddition and the like. For the synthesis of the fullerene dendrimer of the first generation (cf. preparation example 8) according to Scheme 2, the O-benzyl-protected γ-hydroxybutyric acid 2 is condensed with the carboxy-protected γ-aminotriscarboxylic acid [Behera amine, di-t-butyl 4-amino4-(2-t-butyloxycarbonylethyl)heptanedioate 3 (/14/, /15/, /18/) by reaction with condensing agents and activators such as, for example, dicyclohexyl-carbodiimide [DCD], 1-hydroxybenzotriazole [1-OH-BT], but also other carbodiimides, N-hydroxy compounds, and the like. The acid amide [di-t-butyl 4-(4-benzyloxybutyrylamino)4-(2-t-butyloxycarbonylethyl)heptane-dioate 4] resulting therefrom can be deprotected by hydrogenolysis or specific, gentle hydrolysis to give the free hydroxy acid amide [di-t-butyl 4-(4-hydroxybutyrylamino)-4-(2-t-butyloxycarbonylethyl)heptanedioate 5] without affecting the protective groups of the carboxyl functions in the course of this. The following reaction of 5 with malonyl dichloride and pyridine or other nitrogen bases leads to the dendron 6 of the first generation [nomenclature for cascade polymers: 6-cascade:methane[2]:(2-aza-7-oxa-3,8-dioxooctylidyne)

:tert-butyl propanoate], which is a dialkyl malonate ester with amide-like dendron linkage and a $C_4$-long spacer chain between the branching unit and the malonate residue. Correspondingly, by choice of other benzyl-protected ω-hydroxycarboxylic acids 2 such as, for example, 3-hydroxypropionic acid, 5-hydroxyvaleric acid or 6-hydroxyhexanoic acid, the spacer chain can also be shortened or lengthened in any desired manner. According to a process described by us /16/, $C_{60}$ can then be cyclopropanylated in the presence of $CBr_4$ and DBU/methylene chloride using synthon 6. The tert-butyl protective groups of the resulting

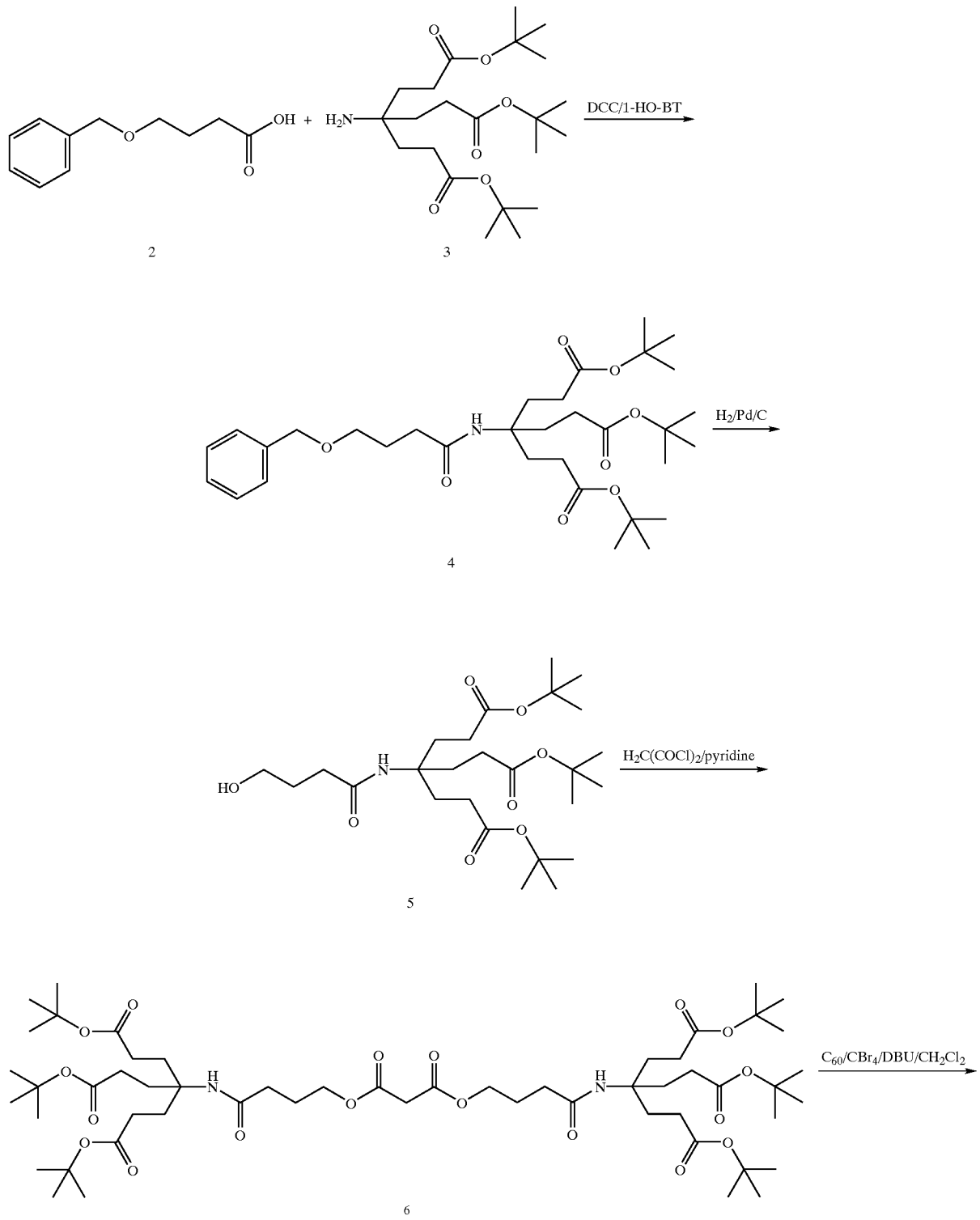

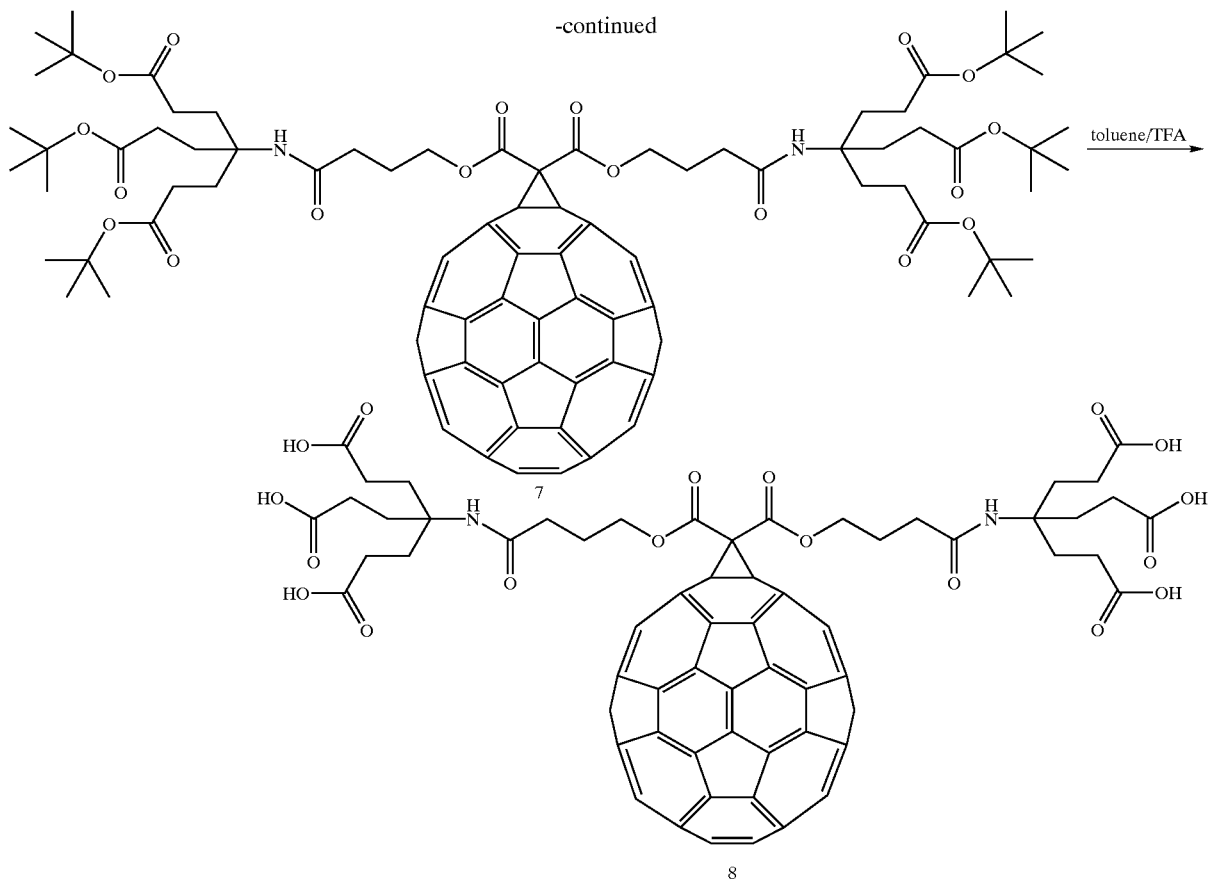

dendrimer fullerene [6-cascade:methano-$C_{60}$-fullerene[2]:(2-aza-7-oxa-3,8-dioxooctylidyne):tert-butyl propanoate 7] can be easily removed by hydrolysis, preferably using formic acid, so that the polycarboxy-functionalized dendrimer fullerene 8 which is water-soluble and can be employed as a neuroprotectant is formed. [6-Cascade:methano-$C_{60}$-fullerene[2]:(2-aza-7-oxa-3,8-dioxooctylidyne):propanoic acid.

The dendrimer fullerene 1 of second generation [18-cascade:methano-$C_{60}$-fullerene[2]:(2-aza-7-oxa-3,8-dioxooctylidyne):(2-aza-3-oxopentylidyne):propanoic acid] (cf. preparation example 1) is prepared (Scheme 3) analogously to the synthesis of the derivative of first generation 8 shown in Scheme 2. As in the first case, the tert-butyl-protected γ-aminotriscarboxylic acid 3 is reacted with the appropriate nitrotriscarboxylic acid 9, whose tert-butyl ester is the synthesis precursor of 3 (15, 16), using DCC in the presence of 1HO-BT and subsequent reduction with hydrogen to the dendron 10 of second generation [9-cascade:aminomethane[3]:(2-aza-3-oxopentylidyne):tert-butyl propanoate]. The analogous reactions as for the preparation of 8 lead to linkage with the spacer 2, formation of the corresponding malonic acid diester and cyclopropanylation to give a carboxyl-protected dendrimer fullerene derivative. The analogous removal of the protective groups leads to the dendrimer fullerene 1 of the second generation. The latter is already very readily soluble in water (pH >7), MeOH and other polar solvents. In water, a solubility of about 34 mg/ml at 25° C. and pH 7 was measured for the compound mentioned. The solubility at pH 10 was about 250 mg/ml.

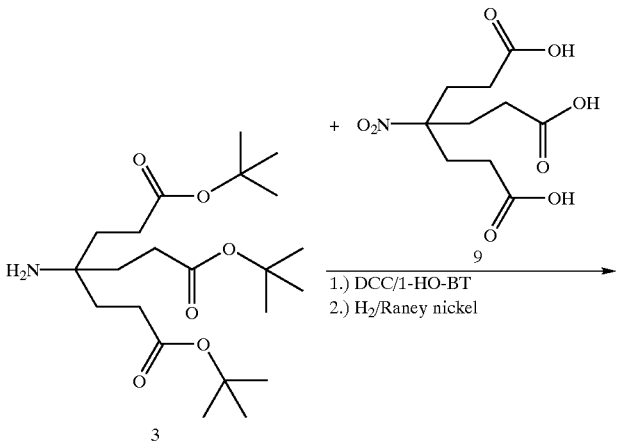

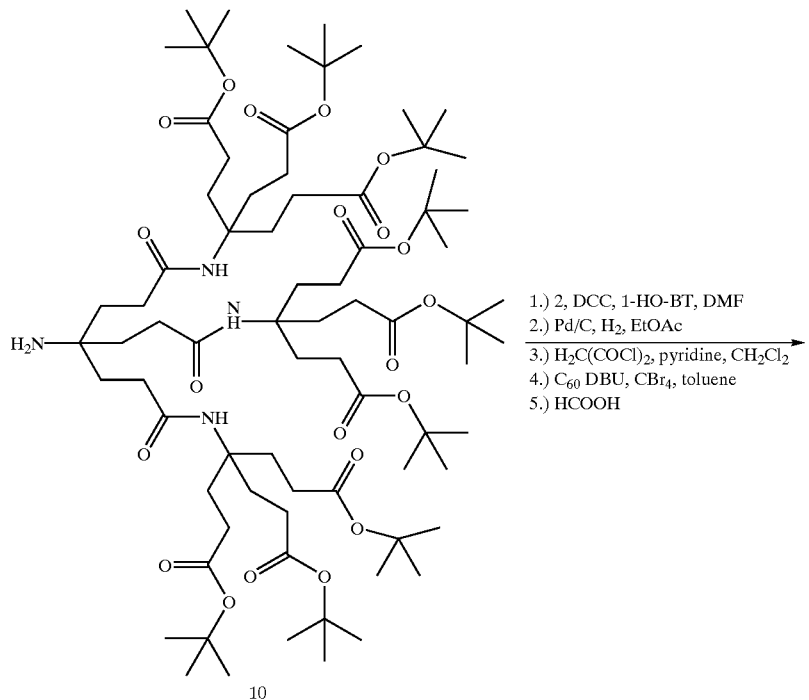

1.) 2, DCC, 1-HO-BT, DMF
2.) Pd/C, H₂, EtOAc
3.) H₂C(COCl)₂, pyridine, CH₂Cl₂
4.) C₆₀ DBU, CBr₄, toluene
5.) HCOOH

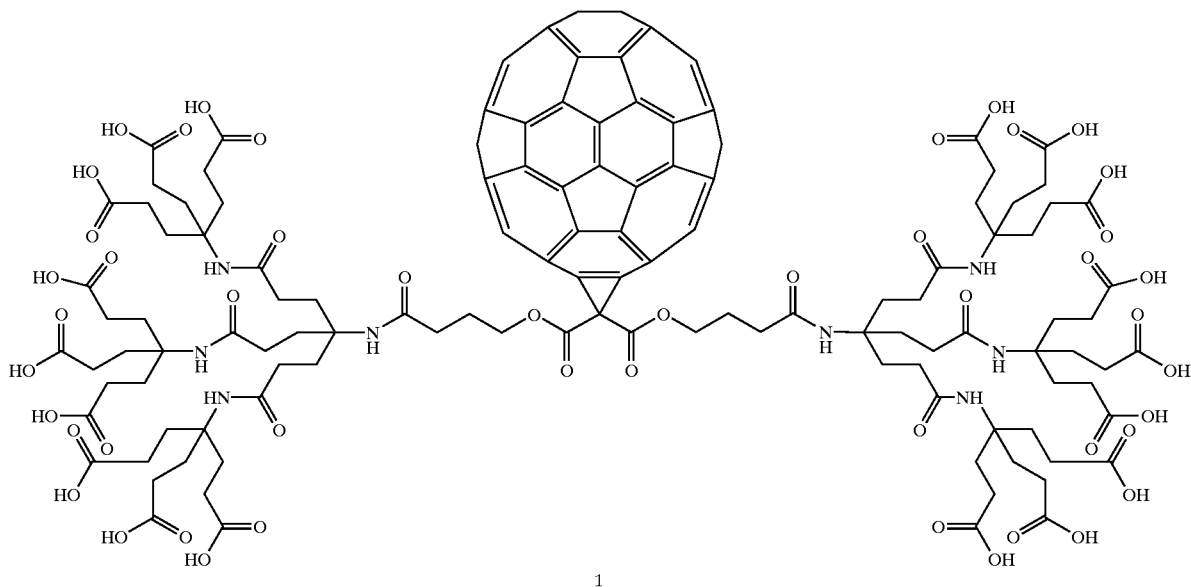

A third condensation reaction between the amino derivative 10 and the nitrotriscarboxylic acid 9 leads to a dendron 11 of the third generation [27-cascade:aminomethane[3]:(2-aza-3-oxopentylidyne)²:tert-butyl propanoate], which in turn can be converted by spacer lengthening into the cyclopropanylation reagent 12 of the third generation. Addition to fullerene $C_{60}$ under the conditions already described yields a dendrimer 13 of the third generation having a $C_{60}$ as core unit. Deprotection of the tert-butyl groups in turn yields a water-soluble dendrimer fullerene [54-cascade:methanofullerene[2]:(2-aza-7-oxa-3,8-dioxooctylidyne):(2-aza-3-oxopentylidyne)²:propanoic acid 14] (Scheme 4) of the third generation, which should be distinguished by radical-scavenging properties and should have membrane-protective and neuroprotective properties.

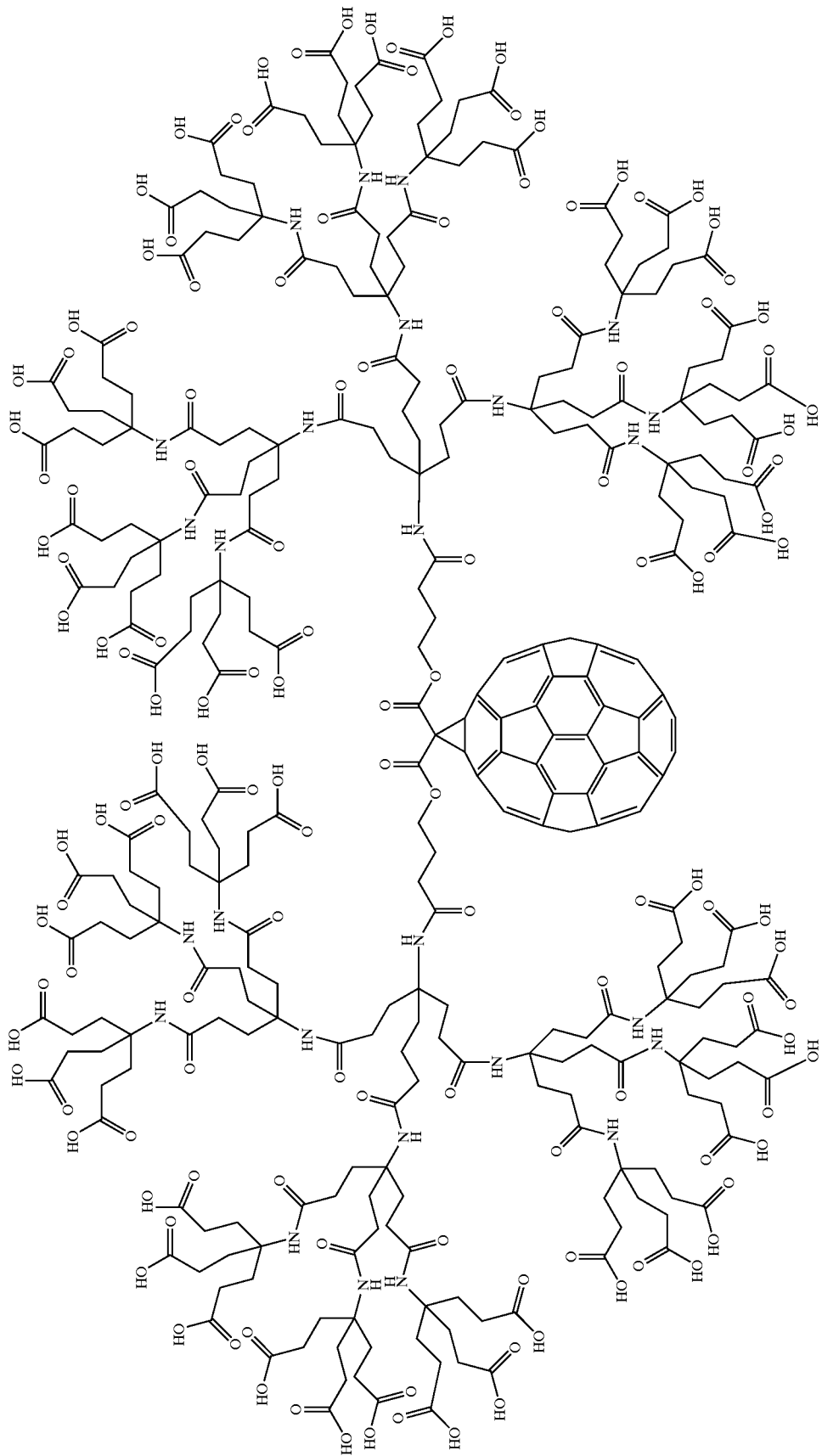
Scheme 4

PREPARATION EXAMPLES

The numbering of the substances results from Scheme 2, the index a designating the appropriate compound of the second generation.

9-Cascade:[N-(4-benzyloxybutyryl)aminomethane][3]:(2-aza-3-oxopentylidyne):tert-butyl propanoate 4a 4.58 g of aminocarboxylic acid ester 10 [9-cascade:aminomethane[3]:2-aza-3-oxopentylidyne):tert-butyl propanoate 10], 618 mg of 4-benzyloxy-butyric acid 2, 656 mg of dicyclohexylcarbodiimide [DCC] and 430 mg of 1-hydroxybenzotriazole [1-HO-BT] are dissolved in 50 ml of DMF and the solution is left stirring for 24 h at room temperature. After removal of the solvent in vac. (in vacuo), the residue is taken up in ethyl acetate and washed with 10% strength cold hydrochloric acid, water, 10% strength NaHCO$_3$ solution and conc. NaCl solution. After drying over MgSO$_4$, the solvent is removed in vac. and the crude product is purified by means of column chromatography (SiO$_2$, hexane/ethyl acetate 1:1). 3.07 g of a white powder (60%) 4a are obtained.

9-Cascade:[N-(4-hydroxybutyryl)aminomethane][3]:(2-aza-3-oxopentylidyne):tert-Butyl propanoate 5a 2.97 g of 4a are dissolved in 100 ml of ethanol and the solution is treated with 100 mg of palladium/carbon (10%). The reaction mixture is hydrogenated at room temperature and normal pressure and after filtering off the catalyst it is concentrated in vac. and 2.66 g (95%) of white powder 5a are obtained.

18-Cascade:methane[2]:(2-aza-7-oxa-3,8-dioxooctylidyne):(2-aza-3-oxopentylidyne):tert-butyl propanoate 6a 1.6 g of 5a and 83 mg of anhydrous pyridine are dissolved in 50 ml of methylene chloride under nitrogen as a protective gas, stirred and cooled to 0° C. 73 mg of malonyl dichloride are slowly added and the mixture is stirred at 0° C. for a further 2 h and at room temperature for 12 h. It is then treated with 50 ml of methylene chloride and washed with water. After drying over MgSO$_4$ and purification by means of column chromatography (SiO$_2$, cyclohexane/ethyl acetate), 425 mg (26%) of product 6a are obtained.

18-Cascade:methano-C$_{60}$-fullerene[2]:(2-aza-7-oxa-3,8-dioxooctylidyne):(2-aza-3-oxopentylidyne):tert-butyl propanoate 7a 425 mg of 6a, 98 mg of C$_{60}$, 45 mg of CBr$_4$ and 23 mg of DBU are dissolved in 100 ml of absolute toluene in a nitrogen atmosphere. The mixture is stirred at room temperature for 22 h, then the solvent is separated in vac. and the residue is purified by means of column chromatography. For this, unreacted C$_{60}$ is first eluted using toluene and then a product mixture using toluene/ethyl acetate (1:1). This is further purified using HPLC. 110 mg (21%) of brown powder 7a are obtained.

18-Cascade:methano-C$_{60}$-fullerene[2]:(2-aza-7-oxa-3,8-dioxooctylidyne):(2-aza-3-oxopentylidyne): propanoic acid 1

100 mg of 7a are dissolved in 15 ml of formic acid and stirred at room temperature. The reaction is complete after 20 h. After removal of the formic acid in an oil-pump vacuum, 70 mg (95%) of a red-brown powder 1 are obtained.

Spectroscopic Data of 1

1: $^1$H-NMR (400 MHz, D$_2$O+K$_2$CO$_3$, 25° C.) δ (ppm) 1.91 (m, 48 H), 2.13 (m, 52 H), 2.47 (t, 4 H), 4.78 (t, 4 H); $^{13}$C-NMR (100 MHz, D$_2$O+K$_2$CO$_3$, 25° C.) δ (ppm) 23.96, 30.95, 31.18, 31.64, 31.87, 32.06, 52.76, 58.21, 58.40, 67.62, 71.53, 138.56, 141.54, 141.79, 142.37, 143.26, 143.52, 143.58, 144.11, 144.47, 145.07, 145.17, 145.22, 145.26, 145.35, 145.60, 145.71, 165.79, 171.45, 174.51, 175.41, 182.78; FT-IR (KBr) v/cm$^{-1}$ 3344, 3074, 2925, 2854, 2625 (broad), 1712, 1654, 1542, 1458, 1414, 1268, 1231, 1206, 1103, 908, 814, 669, 527; UV-Vis (H2O) $\lambda_{max}$ (ε) 257 (102615), 325 (30477), 425 (2077);

LITERATURE REFERENCES

/1/ Krusic, P. J., Wasserman, E., Keizer, P. N., Morton, J. R. and Preston, K. F. (1991), Science, 254, 1183–1185.

/2/ Garthwaite, J., Charles, S. L. and Chess-Williams, R. (1988), Nature (London) 336, 385–388.

/3/ Dawson, V. L., Dawson, T. M., London, E. D., Bredt, D. S. and Snyder, S. H. (1990), Proc. Natl. Acad. Sci. USA 88, 6368–6371.

/4/ Lafon-Cazal, M., Pietri, S., Culcasi, M. and Bockaert, J (1993), Nature (London) 1964, 535–537.

/5/ Dugan, L. L., Sensi, S. L., Canzoniero, L. M. T., Handran, S. D., Rothman, S. M., Lin, T. T., Goldberg, M. P. and Choi, D. W. (1995) J. Neurosci. 15, 6377–6388.

/6/ Reynolds, I. J. and Hastings, G. G. (1995) J. Neurosci. 15, 3318–3327.

/7/ McGeer, E. G. and McGeer, P. L. (1976) Nature (London), 236, 517–524.

/8/ Rothman, S. M. and Olney, J. W. (1986) Ann. Neurol. 19, 105–111.

/9/ Choi, D. W. (1988) Neuron 1, 623–634.

/10/ McIntosh, T. Soares, H., Hayes, R. and Simon, R. (1988) In Frontiers in Exciftatory Amino Acid Research, eds. Cavallo, E. A., Lehman, J. and Turski, L. (Liss., New York) pp. 653–656.

/11/ Dugan, L. L., Gabrielsen, J. K., Yu, S. P., Lin, T. S. and Choi, D. W. (1996) Neurobiol. Dis. 3 129–135.

/12/ Dugan, L. L., Turetsky, D. M., Cheng Du, Lobner, D., Wheeler, M., Almli, C. R., Shen, C. K.-F., Luh, T.-Y., Choi, D. W. and Lin, T.-S. (1997) Proc. Natl. Acad. Sci. USA, 94, 9434–9439.

/13/ Lamparth, I. and Hirsch, A. (1994) J. Chem. Soc. Chem. Commun. 1994, 1727–1728.

/14/ Newkome, G. R., Behera, R. K. Moorefield, C. N. and Baker, G. R. (1991) J. Org. Chem. 56, 7162.

/15/ Newkome, G. R., Nayak, A., Behera, R. K., Moorefield, C. N. and Baker, G. R. (1992) J. Org. Chem. 57, 358.

/16/ Hirsch, A. and Camps, X. (1997) J. Chem. Soc.; Perkin 1 1997, 1595.

/17/ Newkome, G. R., Moorefield, C. N., Vögtle, F., Dendritic Molecules, VCH Weinheim New York Basle Cambridge Tokyo, 1996.

/18/ Camps, X., Schonberger, H. and Hirsch, A. (1997) Chemistry Eur. J. 3, 561.

/19/ J.-F. Nierengarten et al. Helvetica Chimica Acta Vol. 80, (1997), 2238–2276.

What is claimed is:

1. A dendrimeric fullerene derivative, in which the fullerene is linked to at least one dendron, wherein the or each dendron has at least one protic group which imparts water solubility.

2. The fullerene derivative as claimed in claim 1, wherein the number of protic groups which impart water solubility is greater than 4.

3. The fullerene derivative as claimed in claim 1, wherein the or each protic group is identically or differently selected from the group consisting of —OH, —COOH, —NH$_2$, —SO$_3$H, —PO$_3$H, —NR$_4^+$, —NHOH, —SO$_2$NH$_2$, where the four radicals R independently of one another can in each case identically or differently be —H, alkyl or aryl.

4. The fullerene derivative as claimed in claim 1, wherein the branching elements of the or each dendron are identically or differently selected from the group consisting of γ-aminotriscarboxylic acids, α-aminodicarboxylic acids, α-ω-diaminocarboxylic acids, hydroxycarboxylic acids, tartaric acid derivatives, polyphenols, carbohydrate components of the pentose or hexose type and glycerol derivatives.

5. The fullerene derivative as claimed in claim 1, wherein its water solubility is greater than 1 mg/ml at 25° C. and pH 7.

6. A process for the preparation of compounds as claimed in claim 1, which comprises preparing the dendrons in a first step and bonding them to the fullerene via the addenda in a second step.

7. The process as claimed in claim 6, wherein the dendrons are prepared in a convergent synthesis.

8. An agent comprising compounds as claimed in claim 1 for therapeutic purposes.

9. An agent comprising the fullerene as claimed in claim 1, as neuroprotectant.

10. The fullerene derivative as claimed in claim 1, wherein the number of protic groups which impart water solubility is greater than 20.

11. The fullerene derivative as claimed in claim 1, wherein the number of protic groups which impart water solubility is greater than 30.

12. The fullerene derivative as claimed in claim 1, wherein the number of protic groups which impart water solubility is greater than 40.

13. A method of producing pharmaceuticals for the treatment of diseases in which free radicals have a harmful effect on the organism to be treated which comprises incorporating the fullerene derivative as claimed in claim 1 into the pharmaceutical.

* * * * *